United States Patent
Bichkov et al.

(10) Patent No.: US 7,179,843 B2
(45) Date of Patent: Feb. 20, 2007

(54) METHOD OF AND APPARATUS FOR PRODUCING METHANOL

(75) Inventors: Oleg Vitalievich Bichkov, Moscow (RU); Yury Budansky, Oakland, NJ (US); Alexander Leonidovich Tots, Moscow (RU); Vladimir Ivanovich Vedeneev, Moscow (RU)

(73) Assignee: Gas Technologies LLC, Walloon Lake, MI (US)

( * ) Notice: Subject to any disclaimer, the term of this patent is extended or adjusted under 35 U.S.C. 154(b) by 8 days.

(21) Appl. No.: 10/901,717

(22) Filed: Jul. 29, 2004

(65) Prior Publication Data

US 2006/0035986 A1  Feb. 16, 2006

(51) Int. Cl.
*C07C 27/00* (2006.01)
*C07C 45/00* (2006.01)
*C07C 27/10* (2006.01)

(52) U.S. Cl. .............. 518/700; 518/703; 568/482; 568/910

(58) Field of Classification Search ............ 518/700, 518/703; 568/482, 910
See application file for complete search history.

(56) References Cited

U.S. PATENT DOCUMENTS

| 2,196,188 A | 4/1940 | Bone |
| 2,722,553 A | 11/1955 | Mullen |
| 4,152,407 A | 5/1979 | Fuchs |
| 4,243,613 A * | 1/1981 | Brockhaus et al. ......... 568/482 |
| 4,530,826 A | 7/1985 | Ohashi |
| 5,177,279 A | 1/1993 | Harandi |
| 5,959,168 A | 9/1999 | Aalast |

FOREIGN PATENT DOCUMENTS

| GB | 2196335 | 4/1988 |
| RU | 2162460 | 1/2001 |
| RU | 2200731 | 3/2003 |
| SU | 1336471 | 9/1996 |
| SU | 1469788 | 11/1996 |
| WO | WO 96/06901 | 3/1996 |

OTHER PUBLICATIONS

M. M. Karaveav, et al "Technology of Synthetic Methanol", Moscow, Chemistry, 1984 pp. 72-125.

* cited by examiner

*Primary Examiner*—J. Parsa
(74) *Attorney, Agent, or Firm*—Harness, Dickey & Pierce, P.L.C.

(57) ABSTRACT

Production of methanol includes supplying into a reactor a hydrocarbon-containing gas, supplying into the reactor an oxygen-containing as gas, carrying out in the reactor an oxidation of the heated hydrocarbon-containing gas by oxygen of the oxygen-containing gas, and supplying into the reactor a cold hydrocarbon-containing gas to be mixed directly with a mixture of the heated hydrocarbon-containing gas and the oxygen-containing gas at a later stage of the reaction to produce also formaldehyde.

9 Claims, 3 Drawing Sheets

METHOD OF AND APPARATUS FOR PRODUCING METHANOL

BACKGROUND OF THE INVENTION

The present invention relates to a method of and an apparatus for producing methanol.

Methods and apparatuses for conversion of methane into methanol are known. It is known to carry out a vapor-phase conversion of methane into a synthesis gas (mixture of CO and H2) with its subsequent catalytic conversion into methanol as disclosed, for example, in Karavaev M. M., Leonov B. E., et al "Technology of Synthetic Methanol", Moscow, "Chemistry" 1984, pages 72–125. However, in order to realize this process it is necessary to provide a complicated equipment, to satisfy high requirements to purity of gas, to spend high quantities of energy for obtaining the synthesis gas and for its purification, to have a significant number of intermittent stages from the process. Also, for medium and small enterprises with the capacity less than 2000 t/day it is not efficient.

A method for producing methanol is also known which includes a separate supply of a hydrocarbon-containing gas heated to 200–500° C. under pressure 2.15 MPa and an oxygen-containing gas in a mixing chamber, subsequent stages of incomplete oxidation of methane with a concentration of oxygen 1–4 volume percent with an additional introduction of reagents (metal oxide catalyst, higher gaseous hydrocarbons or oxygen-containing compositions, a cold oxidizer) into the reaction zone of a reactor, cooling of the reaction mixture in a heat exchanger, separation of methanol from liquid reaction products in a separator, supply of gaseous waste products to an input of the reactor as disclosed in the Russian patent no. 2,049,086. However, this method requires the use of a catalyst or additional reagents and an intense heating of the reacting gasses, which leads to a decrease of methanol yield and to an increased possibility of soot formation.

A further method of producing methanol is known, which includes a separate supply into a mixer of a hydrocarbon-containing gas (natural gas typically) and an oxygen-containing gas (air or oxygen). This mixture a subsequently supplied into a non-cathalytic reactor for gas phase incomplete oxidation at pressures of 1–10 MPa during up to 1000 seconds at a temperature 300–500° C. without catalyst, return of waste reaction gasses which contain non-reacted methane for mixing with the initial hydrocarbon-containing gas into the first reactor or into the second reactor (which is connected in series with the first reactor), as disclosed in the British patent document GB 2,196,335A. This method provides a high yield of methanol. However, due to significant time of reaction and relatively low per pass conversion (5–15% of methane can reacts during each passage through the reactor) this method has a low efficiency.

A further method of producing methanol by a separate supply and oxidation of hydrocarbon-containing gas and oxygen-containing gas at temperature 370–450° C. and pressure 5–10 MPa and time of contact in the reactor 0.2–0.22 sec is also known, and includes cooling of the heated reaction mixture to 330–340° C., introduction of methanol into the reactor, as disclosed in the patent document of the Soviet Union SU 1,469,788. Cooling of the reaction mixture without intermediate condensation and separation to 380–400° C. in multi-stage heat exchangers arranged in the reactor with subsequent supply of the mixture to 2–3 successive stages of oxidation is disclosed in the patent document of the Soviet Union 1,336,471. In the first case it is necessary to have an additional consumption and a secondary separation of methanol that leads to unavoidable losses, and in the second case it is necessary to provide additional cooling loops with circulation of additional cooling agent in them.

An apparatus for producing methanol is known, which includes a plurality of units arranged after one another and connected by pipes, in particular a mixing chamber connected to separate sources of hydrocarbon-containing gas and air or oxygen, a reactor composed of an inert material with a heating element for incomplete oxidation of methane in a mixture supplied into the reactor under an excessive pressure, a condensor and a separator for separation of methanol from the products of reaction, a vessel for recirculated gaseous reaction products with a pipe for their supply into the initial hydrocarbon-containing gas or mixing chamber as disclosed in the British patent no. 2,196,335A. However, a significant time of presence of the reagents in the reactor reduces efficiency of the apparatus, and makes the process practically unacceptable in industrial conditions.

An apparatus which is close to the present invention is disclosed in Russian patent no. 2,162,460. It includes a source of hydrocarbon-containing gas, a compressor and a heater for compression and heating of gas, a source of oxygen-containing gas with a compressor. It further includes successively arranged reactors with alternating mixing and reaction zones and means to supply the hydrocarbon-containing gas into a first mixing zone of the reactor and the oxygen-containing zone into each mixing zone, a recuperative heat exchanger for cooling of the reaction mixture through a wall by a stream of cold hydrocarbon-containing gas of the heated hydrocarbon-containing gas into a heater, a cooler-condenser, a separator for separation of waste gasses and liquid products with a subsequent separation of methanol, a pipeline for supply of the waste gas into the initial hydrocarbon-containing gas, and a pipeline for supply of waste oxygen-containing products into the first mixing zone of the reactor.

In this apparatus however it is not possible to provide a fast withdrawal of heat of high-thermic volume reaction of oxidation of the hydrocarbon-containing gas, because of inherent limitations of the heat-exchanger. This leads to the necessity to reduce the quantity of supplied hydrocarbon-containing gas and, further it reduces the degree of conversion of the hydrocarbon-containing gas. Moreover, even with the use of oxygen as an oxidizer, it is not possible to provide an efficient recirculation of the hydrocarbon-containing gas due to fast increase of concentration of carbon oxides in it. A significant part of the supplied oxygen is wasted for oxidation of CO into CO2, which additionally reduces the degree of conversion of the initial hydrocarbon-containing gas and provides a further overheating of the reaction mixture. The apparatus also requires burning of an additional quantity of the initial hydrocarbon-containing gas in order to provide a stage of rectification of liquid products with vapor. Since it is necessary to cool the gas-liquid mixture after each reactor for separation of liquid products and subsequent heating before a next reactor, the apparatus is substantially complicated, the number of units is increased, and an additional energy is wasted.

A further method and apparatus for producing methanol is disclosed in the patent document RU 2,200,731, in which compressed heated hydrocarbon-containing gas and compressed oxygen-containing gas are introduced into mixing zones of successively arranged reactors, and the reaction is performed with a controlled heat pick-up by cooling of the reaction mixture with water condensate so that steam is obtained, and a degree of cooling of the reaction mixture is regulated by parameters of escaping steam, which is used in liquid product rectification stage.

Other patent documents such as U.S. Pat. Nos. 2,196,188; 2,722,553; 4,152,407; 4,243,613; 4,530,826; 5,177,279; 5,959,168 and International Publication WO 96/06901 discloses further solutions for transformation of hydrocarbons.

It is believed that the existing methods and apparatus for producing methanol can be further improved.

SUMMARY OF THE INVENTION

It is accordingly an object of the present invention to provide a method of and an apparatus for producing methanol, which is a further improvement of the existing methods and apparatuses.

It is another feature of the present invention to provide a method of and an apparatus for producing methanol which can be used directly on gas and gas-condensate deposits, and also at any gas consumer, such as power plants, gas distributing and gas reducing stations, chemical production facilities, etc.

In keeping with these objects and with others which will become apparent hereinafter, one feature of the present invention resides, briefly stated, in a method of producing methanol, which includes the steps of supplying into a reactor a hydrocarbon-containing gas, supplying into the reactor an oxygen-containing gas; carrying out in the reactor an oxidation of said heated hydrocarbon-containing gas by oxygen of said oxygen-containing gas; and supplying into the reactor a cold hydrocarbon-containing gas to be mixed directly with a mixture of said heated hydrocarbon-containing gas and said oxygen-containing gas at a later stage of the reaction to produce methanol and also formaldehyde.

Another feature of the present invention is an apparatus for producing methanol, which has a reactor for receiving and reacting a hydrocarbon-containing gas with an oxygen-containing gas, to carry out in the reactor oxidation of said heated hydrocarbon-containing gas by oxygen of said oxygen-containing gas; and means for supplying into the reactor a cold hydrocarbon-containing gas to be mixed directly with a mixture of said heated hydrocarbon-containing gas and said oxygen-containing gas at a later stage of the reaction to produce methanol and also formaldehyde.

As can be seen, in accordance with the present invention, heated hydrocarbon-containing gas and air are supplied into a reaction zone or into a reactor, where a gas phase oxidation of the hydrocarbon-containing gas is performed at elevated temperature and pressure in the reaction zone. The reaction mixture is cooled before extraction and the cooled reaction mixture is separated into waste gas and liquid product, the liquid products are rectified with separation of methanol, the waste gas is withdrawn, and a liquid is rectified with production of formalin, wherein cold hydrocarbon-containing gas is supplied into a regulation zone of the reactor to reduce the reaction temperature for example by 70–90° and thereby to provide a production and a redistribution of the ratio of products to produce corresponding quantities of methanol and formaldehyde.

The reaction is performed in a homogenous phase by a partial combustion without presence of a hydrogenous catalyst.

The regulating zone is provided with a device for introduction of non-heated hydrocarbon-containing gas for cooling of the reaction mixture by means of its turbulent mixing with the main stream.

The device for final cooling of the reaction mixture before separation can include a gas-liquid heat exchanger connected with the reactor, a separator and a rectification unit, and a device for cooling, located one after the other.

The inner wall of the reaction zone can be coated with a material which is inert to the reaction mixture. The reactor can be provided with thermal pockets for introducing devices for control of temperature in the reaction zone and for control and regulation in the regulating zone, such as for example thermocouples.

In accordance with a preferred embodiment of the present invention, the required temperature at the inlet of the reactor is provided by heating of the hydrocarbon-containing gas to a needed temperature, for example in a tubular oven.

In accordance with a preferred embodiment of the present invention, the introduction of the cold hydrocarbon-containing gas for reduction of temperature in the regulating zone can be performed by an introducing device and a temperature regulating valve arranged in the introduction line.

In accordance with a preferred embodiment of the present invention, during cooling of the reaction mixture in the gas-liquid heat exchanger, heat is transmitted to the raw methanol supplied into a lower part of the separator, up to a desired temperature for performing rectification the input of the rectification coolant. The final cooling is carried out in the air cooling device. Then, the cooled gas is supplied into separator, in which dry gas, raw methanol and liquid are separated. The raw methanol, through the heat exchanger with temperature 100–120° C. is supplied into a rectification column. The temperature of the top of the column is 70–75° C., the pressure in the column is up to 0.2 Mpa. Methanol with the concentration up to 96% is supplied to a park, while the residue which contains formaldehyde is supplied to the rectification column with temperature at its top up to 80°. The final product is supplied to a park.

The time of presence of the reaction mixture in the reactor is 1.2 sec. The period of induction takes approximately 70% of this time, and thereafter a significant temperature increase of the mixture takes place. The content of methanol in the exiting gas, due to its high stability is 40%, while the content of the formaldehyde is 4%. In order to increase the portion of formaldehyde to 8–13% in the final product, the temperature of the reaction is reduced by 70–80° in the moment of jump after the period of induction at 0.7–1.4 sec of reaction due to the injection of the cold hydrocarbon-containing gas into the regulating zone.

When the temperature of reaction is changed from 370° C. to 450° C., the content of aldehydes is increased from 5% to 13% the content of organic acids is increased from 0.5 to 0.7%. The selectivity which is close to a maximum with respect to liquid organic products, including methanol and formaldehyde, is maintained at a concentration of oxygen in the initial gas mixture 2–2.8%.

In accordance with the present invention, the waste gasses are returned back into the process in the apparatus for gas preparation, without distorting its operation and quality of gas. Also, when the apparatus is arranged at gas power plants, the returned gas does not change its caloric content.

The apparatus is ecologically clean and does not produce hazardous wastes. In contrast, in known apparatuses, it is necessary to burn up to 3 million ton per year of formaldehyde mixture when the capacity of the apparatus 6 million ton per year.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
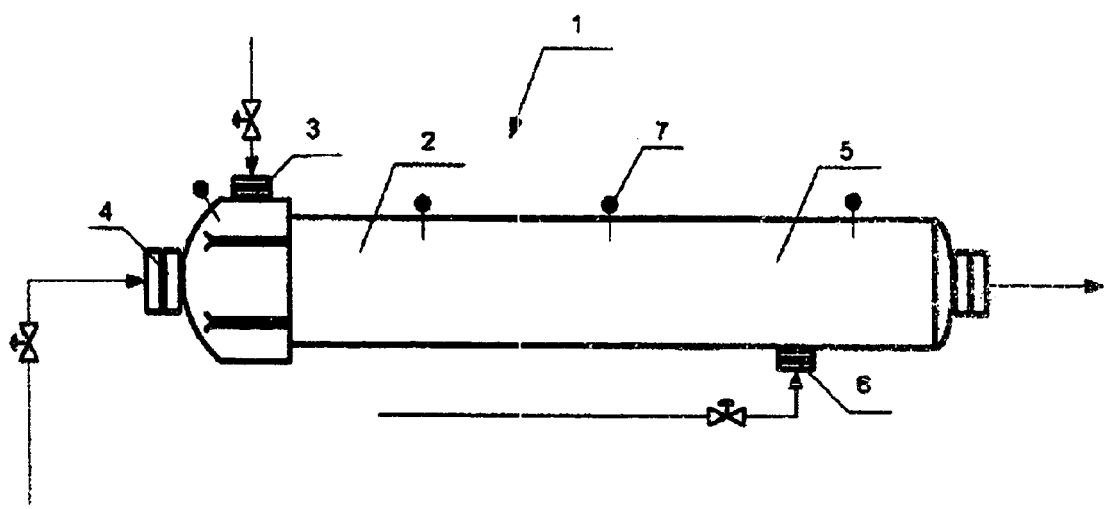
FIG. 1 is a view schematically showing a reactor of an apparatus for producing methanol in accordance with the present invention.

An apparatus for producing methanol in accordance with the present invention has a reactor which is shown in FIG. 1 and identified as a whole with reference numeral 1. In the reactor a gas phase oxidation of a hydrocarbon-containing gas is carried out. The reactor 1 has a reaction zone 2 which is provided with a device 3 for introducing a heated hydrocarbon-containing gas and a device 4 for introducing an oxygen-containing gas, for example air.

The reactor further has a regulation zone 5 provided with a device 6 for introducing a cold hydrocarbon-containing gas, for reducing the temperature of reaction during operation of the apparatus. In addition, the reactor 1 is provided with thermal pockets 7 for control and regulation of temperatures in corresponding zones, provided for example with thermocouples.

Figure 2:
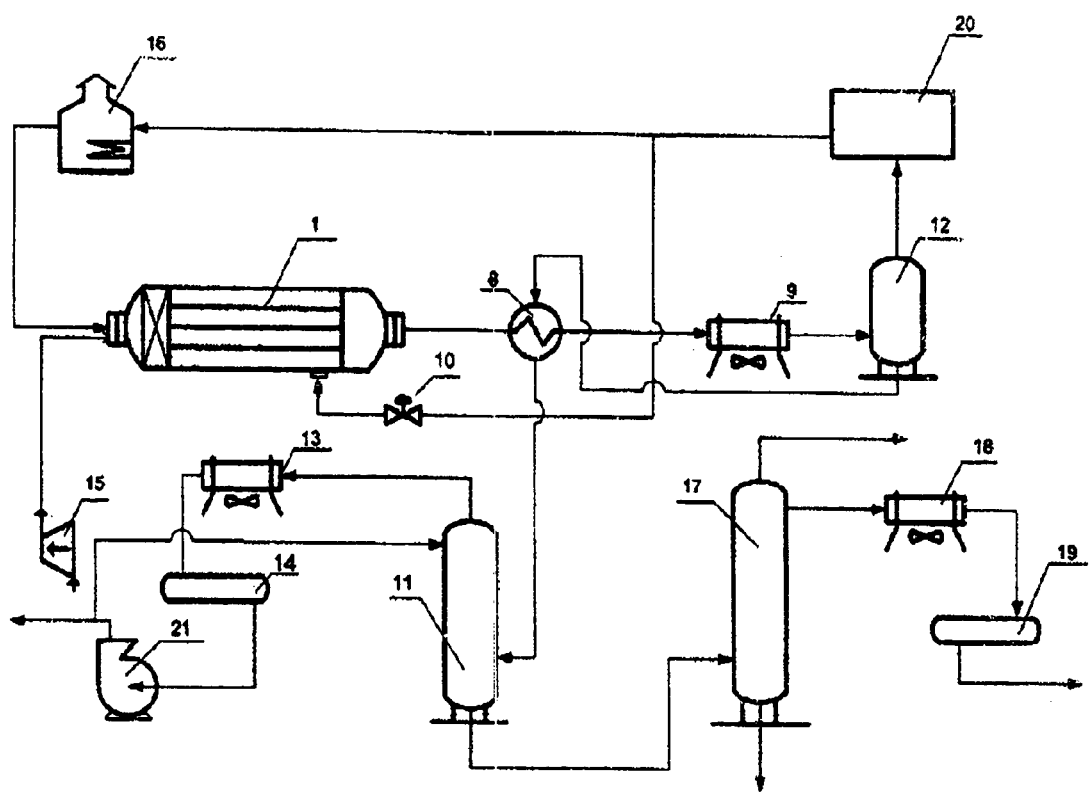
FIG. 2 is a view showing the apparatus for producing methanol, including the reactor and other devices, in accordance with the present invention.

As can be seen from FIG. 2, the apparatus has a device for cooling the reaction mixture before separation, which includes a gas-liquid heat exchanger 8 and an air cooling device 9, as well as a regulator of cold gas supply 10. The gas-liquid heat exchanger 8 is connected with a rectification unit, in particular with a rectification column 11 and a separator 12. The rectification column 11 is connected with an air cooling device 13, which is connected with a vessel 14. Regenerated methanol is supplied from the vessel 14 by a pump 21 to a park.

The reactor 1 is connected with a compressor 15 for supply of compressed air, and with an oven 16 for heating of hydrocarbon-containing gas. The apparatus further has a unit for rectification of formaldehyde which includes a rectification column 17, an air cooling device 18 and a vessel 19, from which formaldehyde is supplied to a park.

In operation, a hydrocarbon-containing gas with a methane content for example up to 98% is supplied from an installation for preparation of gas or any other source 20 to the oven 16, in which it is heated to temperature 430–470° C. Then the heated hydrocarbon-containing gas is supplied into the reaction zone 2 of the reactor 1. Compressed air with pressure for example 8 MPa and with a ratio 1–2.5% of oxygen is supplied by the compressor 15 also into the reaction zone 2 of the reactor 1. Oxidation reaction takes place in the reaction zone of the reactor 1. A second stream of cold or in other words not heated hydrocarbon-containing gas from the same source is supplied through the introducing device 6 into the regulation zone 5 of the reactor 1. This stream is regulated by the regulating device 10, which can be formed as a known gas supply regulating device, regulating valve or the like.

Depending on an intended mode of operation of the apparatus, in particular the intended production of methanol or formaldehyde, the reaction mixture is subjected to the reaction in the reactor without the introduction of the cold hydrocarbon-containing gas if it is desired to produce exclusively methanol, and with the introduction of the cold hydrocarbon-containing gas when it is desired to produce also formaldehyde. By introduction of the cold hydrocarbon-containing gas, the temperature of the reaction is reduced for example by 70–90° so as to increase the content of formaldehyde into the separated mixture.

The reaction mixture is supplied into the heat exchanger 8 for transfer of heat to the raw methanol from the separator 12, and after final cooling in the air cooling device 9 is supplied with temperature 20–30° C. to the separator 12. Separation of the mixture into dry gas and raw methanol is performed in the separator 12. The dry gas is returned to the source 20, while the raw methanol through the gas-liquid heat exchanger 8 is supplied to the rectification column 11. From the rectification column 11 vapors of methanol through the air cooling device 13 are supplied into the vessel 14. Regenerated methanol is supplied by a pump 21 to a park. A part of methanol is supplied from the vessel 14 for spraying of the rectification column 11.

The method in accordance with the present invention and the operation of the apparatus in accordance with the present invention are illustrated by an example of operation of the apparatus with the capacity of 6,000 t/year, with cooling of the reaction mixture by 30° C.

TABLE 1

| Parameters | Example 1 without cooling | Example 2 with cooling by 30° C. |
|---|---|---|
| Natural gas supply, m³/hour (kg/hour) | 56800 (40570) | 60208 (43004) |
| Gas consumption in reaction, m³/hour (kg/hour) | 1700 (1215) | 1700 (1215) |
| Conversion degree, % | 3 | 3 |
| Oxygen concentratino in reaction entry zones, % | 2 | 2 |
| Pressure in reactor, MPa | 7 | 7 |
| Cooling in regulation zone | no cooling | direct mixing with cold gas |
| Methanol yield, kg/hour | 800 | 800 |
| Formaldehyde yield, kg/hour | 115 | 230 |
| Total organic products yield, kg/hour | 920 | 1040 |
| Initial temperature, ° C. | 450 | 450 |
| Reaction temperature, ° C. | 530 | 530 |
| Temperautre in regulation zone, ° C. | 530 | 500 |

Figure 3:
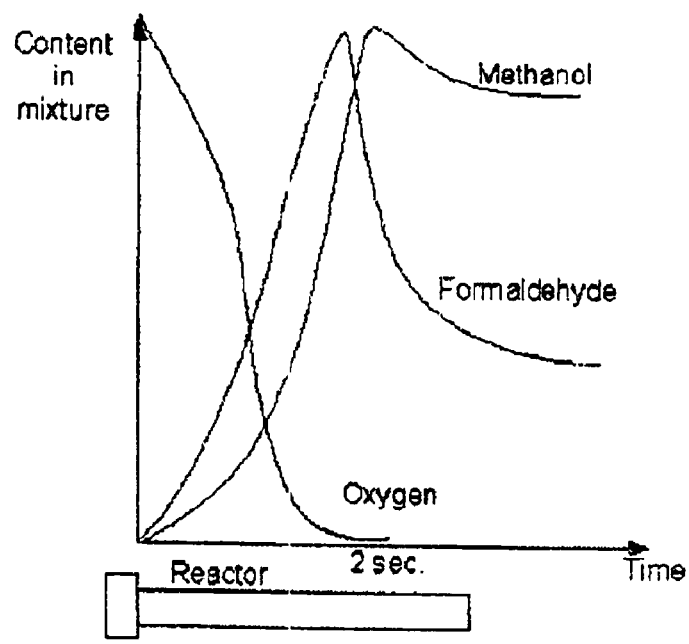
FIGS. 3 and 4 are views illustrating concentrations of oxygen, formaldehyde and methanol during reactions in accordance with the prior art and in accordance with the present invention correspondingly.
Figure 4:
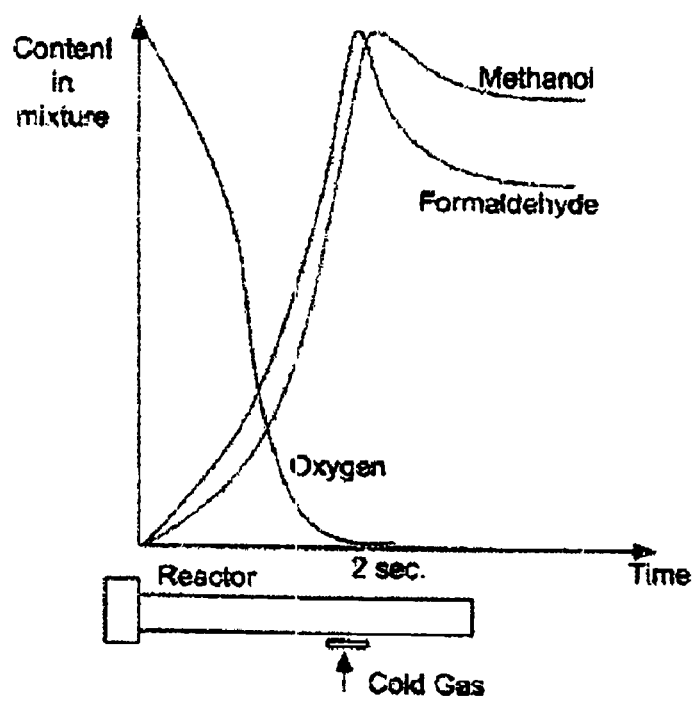

FIGS. 3 and 4 show diagrams of concentration of oxygen, formaldehyde and methanol in reactions without cooling and with cooling.

As can be seen from FIG. 3, approximately after 2 sec, oxygen is burnt completely. At this moment the reaction temperature reaches its maximum, and in the reaction mixture methanol and formaldehyde are produced with their proportions. Methanol as a more stable product at the end of the reaction reaches its maximum concentration and maintains it practically stable. Formaldehyde is less stable, and therefore with a temperature increase (the temperature increases until oxygen is burnt completely) its concentration somewhat reduces.

In the reaction with the cooling shown in FIG. 4, with introduction of the cold gas when the formation of methanol and formaldehyde is completed, the temperature of a final period of the reaction is reduced, so that formaldehyde can not decompose and reduce its concentration. Since methanol remains stable, its concentration remains constant (see Table), while content of formaldehyde increases (on the account of other reaction products).

It will be understood that each of the elements described above, or two or more together, may also find a useful application in other types of methods and constructions differing from the types described above.

While the invention has been illustrated and described as embodied in method of and apparatus for producing methanol, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The invention claimed is:

1. A method of producing methanol, comprising the steps of:
   supplying into a reactor a heated hydrocarbon-containing gas;
   supplying into the reactor an oxygen-containing gas;
   carrying out in the reactor an oxidation of the heated hydrocarbon-containing gas by the oxygen-containing gas; and
   supplying into the reactor at a location of said reactor where the oxidation reaction has advanced substantially, a cold hydrocarbon-containing gas to be mixed directly with a mixture of the hydrocarbon-containing gas and the oxygen-containing gas to impede the decomposition of formaldehyde.

2. The method as defined in claim 1, further comprising performing the reaction in a homogeneous phase by a partial combustion without presence of a heterogeneous catalyst.

3. The method as defined in claim 1, further comprising preheating of the hydrocarbon-containing gas before the supplying it into the reactor.

4. The method as defined in claim 1, wherein said supplying of the hydrocarbon-containing gas and said supplying of the cold hydrocarbon-containing gas includes taking a hydrocarbon-containing gas from a single source, heating one portion of the hydrocarbon-containing gas taken from the source to produce the heated hydrocarbon-containing gas for supplying into the reactor; and supplying another portion of the hydrocarbon-containing gas from the same source as the cold hydrocarbon-containing gas into the reactor.

5. The method as defined in claim 1, wherein said supplying of the cold hydrocarbon-containing gas into a reactor at a later stage includes supplying the cold hydrocarbon-containing gas into the reactor at the stage when formation of methanol and formaldehyde is substantially completed.

6. The method as defined in claim 1, wherein said supplying of the cold hydrocarbon-containing gas includes regulating a quantity of the cold hydrocarbon-containing gas so as to produce a desired quantity of methanol and a desired quantity of formaldehyde in the reactor.

7. The method as defined in claim 4, further comprising cooling a reaction mixture which is received from the reactor and separating from the cooled reaction mixture a hydrocarbon-containing gas for supplying back to the source, and a methanol-containing fraction for obtaining methanol from the methanol-containing fraction.

8. The method as defined in claim 7, wherein said cooling of the reaction mixture includes a heat-exchange between the reaction mixture which left the reactor and a supply of hydrocarbon-containing gas to form the heated hydro-carbon containing gas.

9. The method as defined in claim 8, wherein said cooling of the reaction mixture received from the reactor includes cooling of the reaction mixture by said heat exchange and a subsequent air cooling.

* * * * *